(12) United States Patent
Rodriguez Izal et al.

(10) Patent No.: US 10,473,708 B2
(45) Date of Patent: Nov. 12, 2019

(54) METHODS AND SYSTEMS FOR REAL-TIME MONITORING OF THE INSULATION STATE OF WIND-POWERED GENERATOR WINDINGS

(71) Applicant: GAMESA INNOVATION & TECHNOLOGY, S. L., Sarriguren (Navarra) (ES)

(72) Inventors: Jose Luis Rodriguez Izal, Sarriguren (ES); Isaac Gude Rodriguez, Madrid (ES); Guillermo Sanchez Vitorica, Zamudio (ES); Almudena Munoz Babiano, Madrid (ES)

(73) Assignee: GAMESA INNOVATION & TECHNOLOGY, S.L., Sarriguren (Navarra) (ES)

( * ) Notice: Subject to any disclaimer, the term of this patent is extended or adjusted under 35 U.S.C. 154(b) by 0 days.

(21) Appl. No.: 15/339,074

(22) Filed: Oct. 31, 2016

(65) Prior Publication Data

US 2017/0153286 A1 Jun. 1, 2017

(30) Foreign Application Priority Data

Nov. 26, 2015 (ES) .................................. 201500845

(51) Int. Cl.
*G01R 31/12* (2006.01)
*G01R 31/34* (2006.01)
*G01N 29/44* (2006.01)

(52) U.S. Cl.
CPC ..... *G01R 31/1272* (2013.01); *G01N 29/4445* (2013.01); *G01R 31/343* (2013.01)

(58) Field of Classification Search
CPC .............. G01R 31/1272; G01R 31/343; G01N 29/4445; F03D 17/00; F03D 9/25; G01H 1/003

See application file for complete search history.

(56) References Cited

U.S. PATENT DOCUMENTS

| | | | |
|---|---|---|---|
| 6,981,416 B2 * | 1/2006 | Chen ..................... | G01P 15/125 73/510 |
| 7,677,869 B2 * | 3/2010 | Martinez De Lizarduy Romo ..... | G01H 1/006 416/36 |

(Continued)

FOREIGN PATENT DOCUMENTS

EP 1 531 376 A1 5/2005

*Primary Examiner* — Jennifer E Simmons
*Assistant Examiner* — Leo T Hinze
(74) *Attorney, Agent, or Firm* — Ladas & Parry LLP (57) ABSTRACT

The invention provides methods and systems for real-time monitoring of the insulation state of wind-powered generator windings comprising the following steps: a) capturing in real-time, during a predetermined time period (in situations where the generator is synchronized to the electrical network but is not yet couplet thereto as well as in situations where the generator is producing energy) the values of one or more electrical and vibration variables of the generator; b) obtaining in real-time, the temporal evolution of the vibration and of the inverse components of electrical variables at one or more predetermined frequencies; c) identifying a possible generator insulation fault when the inverse component of at least one electrical variable and/or one vibration at a predetermined frequency exceeds an absolute threshold or a temporal increase threshold pre-sets.

10 Claims, 4 Drawing Sheets

(56) References Cited

U.S. PATENT DOCUMENTS

| | | | |
|---|---|---|---|
| 7,692,324 B2* | 4/2010 | Malakhova | F03D 7/047 290/44 |
| 8,676,386 B2* | 3/2014 | Klodowski | G01R 31/343 700/276 |
| 2007/0140847 A1* | 6/2007 | Martinez De Lizarduy Romo | G01H 1/006 416/11 |
| 2013/0054043 A1* | 2/2013 | Klodowski | G01R 31/343 700/293 |
| 2014/0109679 A1* | 4/2014 | Rodriguez | G01H 1/003 73/660 |
| 2015/0042092 A1* | 2/2015 | Nelson | H02J 3/386 290/44 |

* cited by examiner

METHODS AND SYSTEMS FOR REAL-TIME MONITORING OF THE INSULATION STATE OF WIND-POWERED GENERATOR WINDINGS

FIELD OF THE INVENTION

This invention relates to wind turbines and more particularly to methods and systems for monitoring the insulating state of their generator windings.

BACKGROUND

In order to maximize energy production and avoid unscheduled stops in large plants producing electricity there are different techniques and systems for assessing the insulation state of their generator. These technique and/or systems use special equipment so that when facing an incipient failure in the generator electrical insulation an appropriate corrective maintenance can be programmed.

As in other industrial sectors, in the wind industry would be advisable to monitor the insulation state of generators to avoid the negative consequences that occur in case of failure. In a wind turbine a failure in the generator insulation makes necessary a replacement thereof due to the difficulty for carrying out its on-site repair. Furthermore, in the case of wind power, wind turbines are often installed in places far from an industrial environment and, thus, a generator replacement involves a long repair time and a considerable loss of energy produced.

However the techniques used for assessing the generator insulation state in other industrial sector such as, for example, the electrical generators of conventional thermal or hydroelectric plants are not applicable to wind turbines. The reason is that conventional plants are equipped with a generator of high power, for example 50MVA and above, while a wind farm of the same power can be formed by several wind turbines with generators having a power lesser than 10MVA. Therefore, to detect generator insulation faults in a wind farm, a fault detection system should be installed in each generator increasing significantly the system cost.

In other words, those methods that require the use of specific equipment to monitor the status of each generator in a planned manner throughout its lifetime are not profitable in the wind industry.

It would be, therefore, desirable for the wind industry methods and systems specifically designed to detect insulation failures of wind turbine generators not needing to incorporate additional elements for that task as well as to their integration into existing wind turbines so that their cost is not increased.

The present invention is directed to the attention of these demands.

SUMMARY OF THE INVENTION

In one aspect, the invention provides a method for detecting faults in the insulation of a generator of a wind turbine coupled to an electrical network via a converter and provided with means for measuring electrical variables of the generator (voltage and current in rotor and stator) as well as their radial-horizontal and radial-vertical vibrations in the coupling side and in the opposite side to it.

The method comprises the following steps: a) capturing in real-time, during a predetermined time period (in situations where the generator is synchronized to the electrical network but is not yet couplet thereto as well as in situations where the generator is producing energy) the values of one or more generator electrical variables and/or the values of the generator radial-horizontal and radial-vertical vibrations in at least one of its two coupling sides; b) obtaining in real-time, the temporal evolution of the inverse components of said electrical variables at one or more predetermined frequencies and/or the temporal evolution of the values of said vibrations at one or more predetermined frequencies; c) identifying a possible generator insulation fault when the inverse component of at least one electrical variable and/or one of said vibrations at a predetermined frequency exceeds an absolute threshold or a temporal increase threshold pre-sets.

Embodiments of the method for different types of generator (doubly fed, permanent magnet and squirrel cage) in the mentioned coupling situations to the electrical network are envisaged and the relevant variables and predetermined frequencies for each of them are described.

In another aspect, the invention provides a system for implementing said method comprising a computer system connected to the data bus of the wind turbine for capturing the measures of the electrical variables (which can be provided by the converter or by a separate device thereof) and of the vibration variables provided by a measurement device connected to a set of sensors arranged on the generator.

Other characteristics and advantages of the present invention will be clear from the following detailed description of embodiments illustrative of its object in relation to the attached figures.

DETAILED DESCRIPTION OF THE INVENTION

The present invention provides methods and systems for detecting the state of the insulation of the windings of a wind turbine generator by means of a real-time monitoring of, on the one hand, electrical variables and, on the other hand, its vibration, thereby enabling performing preventive maintenance work to avoid catastrophic failures in the generator insulation.

It has been noted in this regard that an insulation fault in the generator produces an imbalance in their voltages and currents in the rotor and in the stator leading to an increase in the inverse component of said variables particularly at certain frequencies.

Figure 1:
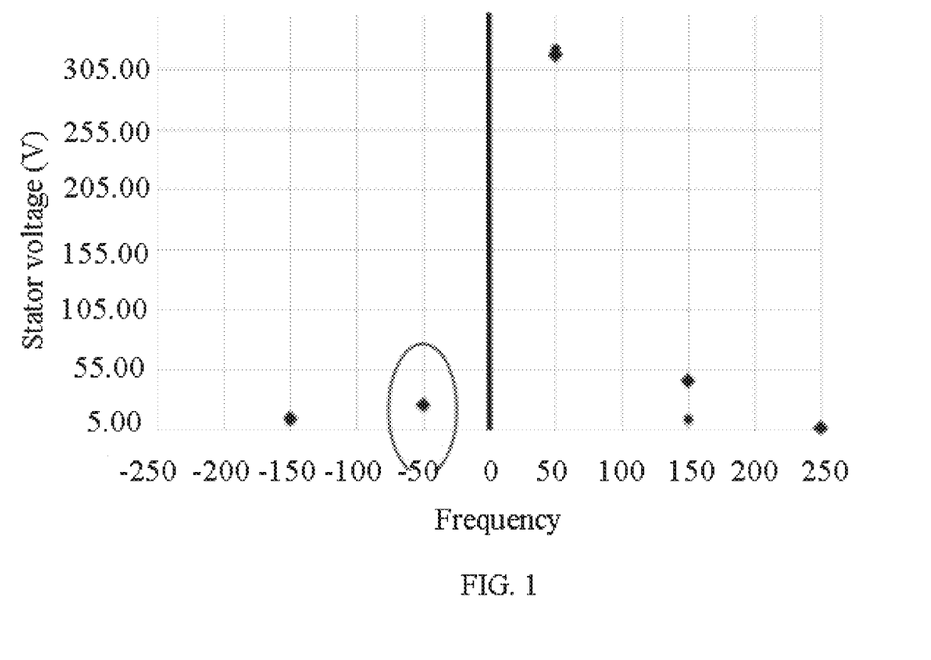
FIG. 1 shows a Fast Fourier Transform containing the reverse (or negative) and direct (or positive) sequence of the stator voltage of a doubly fed wind-powered generator illustrating fault cases with a rhombus and cases without failure with a circle.

For example, when analysing the reverse and the direct sequence of the stator voltage of a doubly fed generator (see FIG. 1) it can be seen that failure occurs when the inverse component of the stator voltage at −50 Hz stator reaches a certain value.

The monitoring of electrical variables proposed by the invention involves three steps:

Capturing in real-time, during a predetermined time period, measurements of the values of one or more electrical variables of the generator (which, as discussed below, can be performed in the converter by which the generator is coupled to the electrical network or in a specific device separated from it).

Figure 2A:
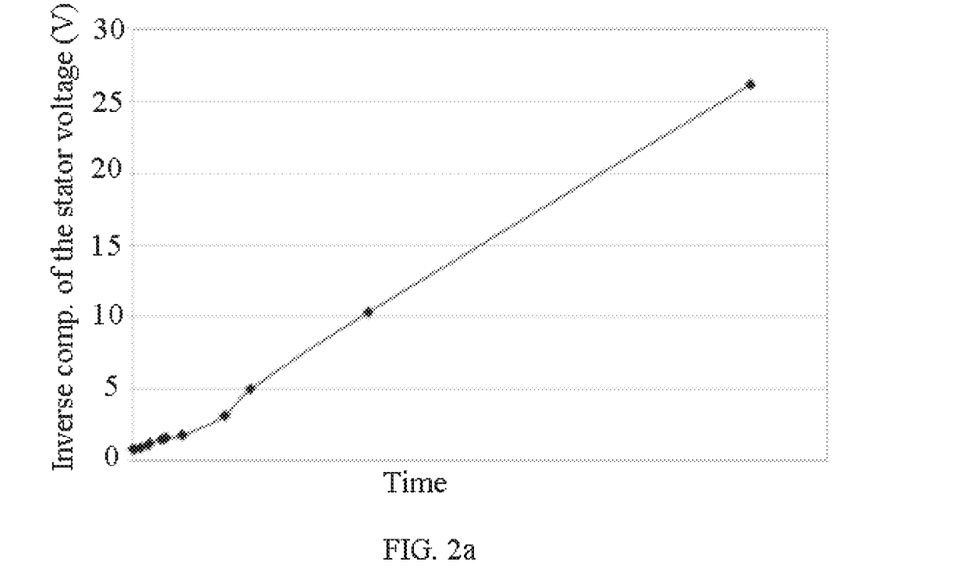
FIG. 2a is a diagram showing the temporal evolution of the inverse component of the stator voltage of a doubly-fed wind-powered generator at −50 Hz and FIG. 2b is the same diagram indicating the absolute threshold and the temporal increase threshold used as fault indicators.

Obtaining in real time, from the measurements of voltage and/or current in the rotor and/or stator of the generator, the temporal evolution of the inverse components of one or more electrical variables at one or more predetermined frequencies where it is considered that there may be a fault in the generator. Following the case shown in FIG. 1, once it has been identified that in a doubly fed generator a failure occurs in the inverse component of the stator at −50 Hz, the temporal evolution of said variable must be obtained. As shown in FIG. 2a the value of the inverse component of the stator voltage at −50 Hz increases over time depending on the severity of the short-circuit.

Figure 2B:
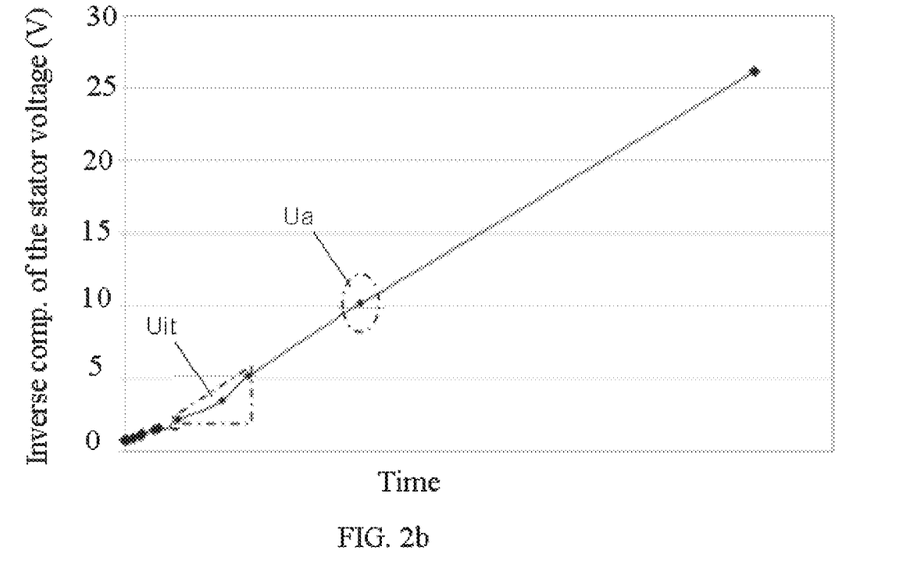

Identifying a possible insulation fault in the generator when the inverse component of, at least, one electric variable at a given frequency exceeds an absolute threshold or a temporal increase threshold pre-sets. Following the example of FIG. 2a and as illustrated in FIG. 2b such a possibility of failure would be identified when:

a) The absolute threshold Ua of the inverse component of the stator voltage reaches the value of 10V.

b) The temporal increase threshold Uit reaches a pre-set value. This value would be reached when the inverse component of the stator voltage reaches the value of 5 v as in the range 2.5-5 v the derivative of the function representing the temporal evolution of the inverse component of the stator voltage reaches high values.

Figure 3:
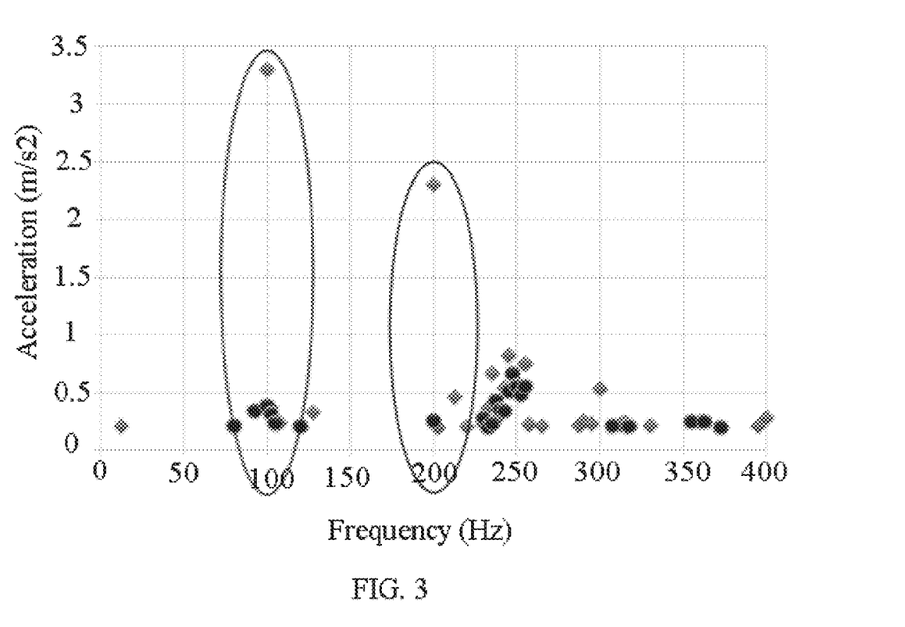
FIG. 3 is a diagram showing comparatively the vibration components of a doubly fed wind-powered generator illustrating fault cases with a rhombus and cases without failure with a circle.

It has also been found that an imbalance of currents caused by a fault in the insulation produces an electromagnetic imbalance that will result in vibration of the generator at a certain frequency. For example, when analysing the evolution of the vibration of a doubly-fed generator of 11 kW it can be seen (see FIG. 3) that there is an increase of vibration at 100 Hz and 200 Hz (2 and 4 times the frequency of a 50 Hz electrical network) when there is an incipient short-circuit in the generator stator.

The monitoring of the vibration proposed by the invention involves three similar steps to those of the electrical variables:

Capturing in real-time, during a predetermined time period, measurements of the radial-horizontal vibration and the radial-vertical vibration of the generator on the side of the coupling to the electrical network and on the side opposite to it which, as will be discussed below, are performed by vibration measuring means incorporated to the generator such as those described in EP 1 531 376 B1.

Obtaining in real-time, from these measurements, the temporal evolution of said vibrations at one or more predetermined frequencies where it is considered that there may be a fault in the generator.

Identifying a possible insulation fault in the generator when at least one of said vibrations at a certain frequency exceeds an absolute threshold or a temporal increase threshold pre-sets.

Once identified a possible insulation fault because any one of the electrical or vibration mentioned variables exceeds any of the above mentioned thresholds appropriate corrective measures would be activated.

Said monitoring will be performed in time periods corresponding to low wind situations in which the generator is synchronized to the electrical network but not coupled thereto and in energy production periods.

In the first case, the objective is to verify the correct state of the insulation before coupling to the electrical network. This will prevent coupling the generator to the electrical network in case of significant loss of insulation and also minimizing the damages occurring in the generator in case of an outright short circuit. Damage or fatigue to other components will be also prevented as high currents or pairs of high short-circuits especially in double-fed generators are avoided. Checking the state of insulation in low wind situations is more effective as both transient events produced in the electrical network and unexpected wind gusts may cause erroneous measurements. Consequently, insulation faults can be detected in more incipient stages, because the lack of transient events allows refining the detection system.

In the second case, the objective is to detect loss of insulation in operation. In this case the generator can be stopped and the condition of the insulation in the previous mode be checked.

Figure 4:
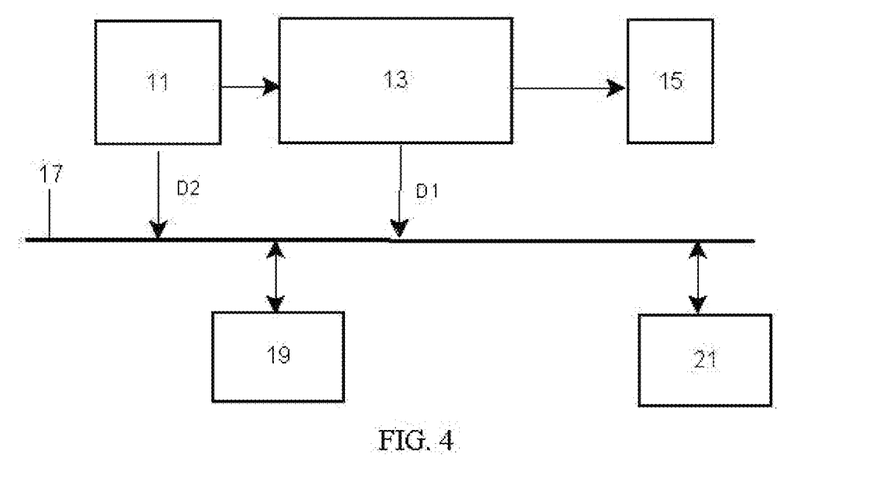
FIG. 4 is a schematic diagram of the fault detection system in the insulation of a wind-powered generator according to the invention.

Following FIG. 4 it can be seen that the mentioned monitoring in a generator 11 of a wind turbine connected to an electrical network 15 via a converter 13 is performed in an external computer system 21 connected to the data bus 17 of the wind turbine to which its control system 19 is also connected.

The data bus 17 receives in real-time a data stream D1 of measurements of the mentioned electrical variables and a data stream D2 of measurements of the mentioned vibrations.

Figure 5:
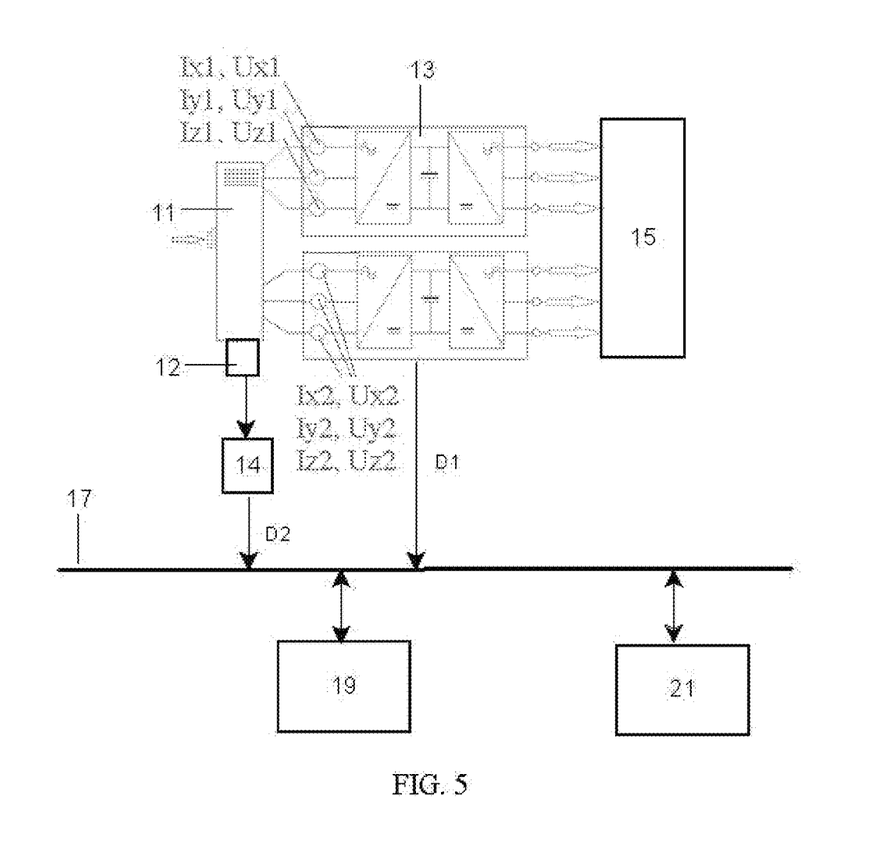
FIGS. 5 and 6 are schematic diagram of two embodiments of the fault detection system in the insulation of a permanent magnets wind-powered generator according to the invention.
Figure 7:
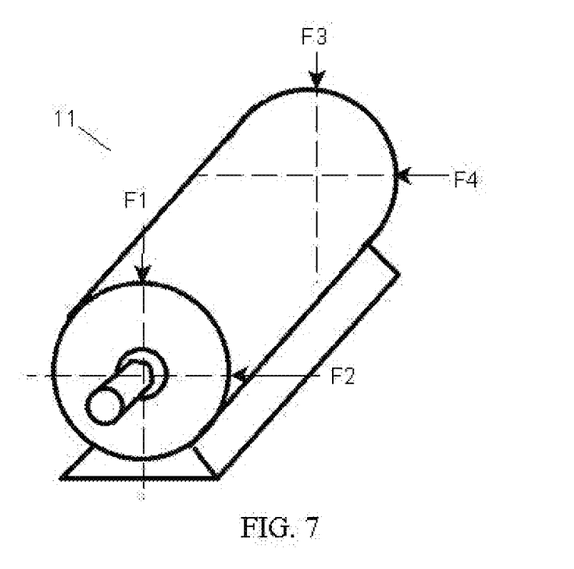
FIG. 7 illustrates the position of radial-vertical and radial-horizontal vibration sensors arranged in a wind-powered generator on the coupling side (the generator shaft exit side) and on the opposite side to the coupling.

As illustrated in more detail in FIG. 5 the data stream D2 of measurements of vibration is generated on a vibration measuring device 14 connected to a sensor assembly 12 arranged on the generator 11. This assembly may comprise (see FIG. 7) sensors in the positions indicated by arrows F1 and F3 for measuring the radial-vertical vibration and by arrows F2 and F4 for measuring the radial-horizontal vibration in, respectively, the coupling side of generator 11 and the side opposite.

Figure 6:
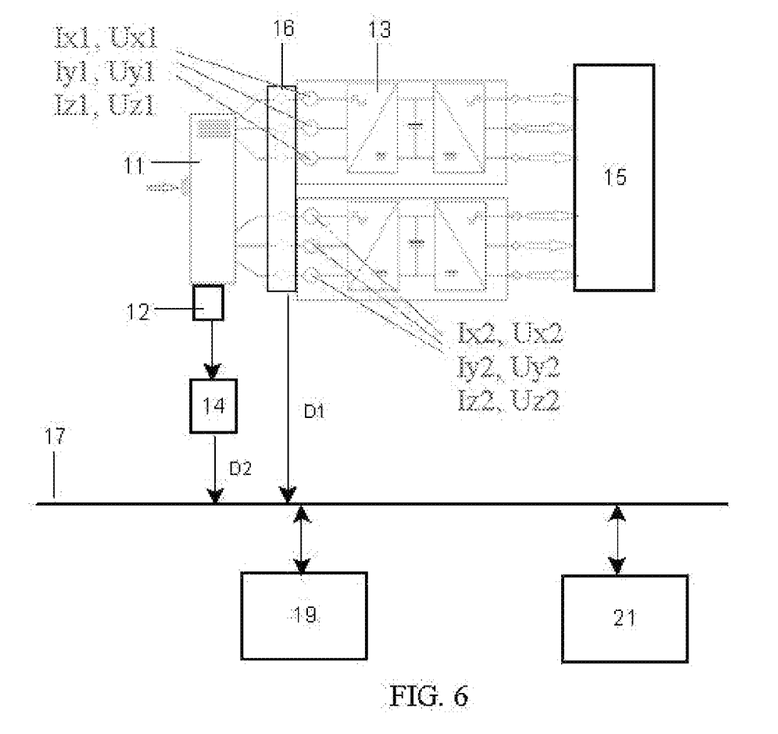

Meanwhile, as illustrated in FIG. 6, the data stream D1 can be generated in a measuring device 16 separated from the converter 13 and provided with means for measuring the electrical variables of generator 11.

The software of the computer system 21 would obtain in real-time the temporal evolution of the inverse component of the mentioned electrical variables and of the mentioned vibrations at the indicated frequencies from data streams D1, D2. Furthermore, through the analysis of their temporal evolution, it would identify a possible failure of the insulation of generator 11 when the value of the inverse component of an electric variable and/or the value of one of the mentioned vibrations of generator 11 exceeds any of the pre-set thresholds. Finally, it would execute the foreseen appropriate alarm and message measures so that when a possible insulation failure is detected appropriate corrective actions can be taken.

The computer system 21 can be used for monitoring the insulation condition of the generator of various wind turbines by accessing their data buses.

The system of the invention is thus applicable to wind turbines having means for supplying in real-time values of the mentioned variables to a computer system 21.

The specific variables to be monitored, depending on the type of generator and on the temporal period in which monitoring is performed, comprise one or more of the following.

A) Doubly Fed Generators a1) The inverse component of the stator voltage at one or more of the following frequencies: frequency of the electrical network, an integer multiple of the inverse component of the frequency of the electrical network, an integer multiple of the direct component of the frequency of the electrical network.

a2) The inverse component of the stator current at one or more of the following frequencies: frequency of the electrical network; an integer multiple of the inverse component of the frequency of the electrical network; an integer multiple of the direct component of the frequency of the electrical network (only when the generator is coupled to the network).

a3) The inverse component of the rotor voltage at one or more of the following frequencies at a given speed (a speed should be selected for processing the measurements at that speed because the fundamental frequency of the rotor varies with its rotation speed): fundamental frequency of the rotor; an integer multiple of the inverse component of the fundamental frequency of the rotor; an integer multiple of the direct component of the fundamental frequency of the rotor.

a4) The inverse component of the rotor current at one or more of the following frequencies at a given speed (a speed shall be selected for processing the measurements at that speed because the fundamental frequency of the rotor varies with its rotation speed): fundamental frequency of the rotor; an integer multiple of the inverse component of the fundamental frequency of the rotor; an integer multiple of the inverse component of the frequency of the electrical network; an integer multiple of the direct component of the frequency of the electrical network; frequencies defined by the formula $+nf_{sw} \pm mf_{rotor}$, being n and m integer numbers, $f_{sw}$ the switching frequency of the converter and $f_{rotor}$ the fundamental frequency of the rotor.

a5) The vibrations mentioned at one or more of the following frequencies: frequencies multiple of the frequency of the electrical network; frequencies defined by the formula $$f_{red}\left[\pm 1 + \frac{\pm gQ}{p}(1-s)\right],$$

being $f_{red}$ the fundamental frequency of the electrical network, g an integer, Q the number of slots of the stator or the rotor (two calculations must, thus, be performed: one for the stator and one for the rotor), p the number of pole pairs y s the slip of the generator (as the slip of the generator varies with the rotational speed, a speed shall be selected for processing the measurements at that speed).

B) Permanent Magnet generators b1) The inverse component of the stator voltage at one or more of the following frequencies: fundamental frequency of the stator; an integer multiple of the inverse component of the fundamental frequency of the stator; an integer multiple of the direct component of the fundamental frequency of the stator.

b2) The inverse component of the stator current at one or more of the following frequencies: fundamental frequency of the stator; an integer multiple of the inverse component of the fundamental frequency of the stator; an integer multiple of the direct component of fundamental frequency the stator; frequencies defined by the formula $\pm nf_{sw} \pm mf_{stator}$, being n and m integer numbers, $f_{sw}$ the switching frequency of the converter and $f_{stator}$ the fundamental frequency of the stator.

b3) The mentioned vibrations at one or more of the following frequencies: frequencies multiple of the frequency of the electrical network; frequencies defined by the formula $$f_{stator}\left[\pm 1 + \frac{\pm gQ}{p}(1-s)\right],$$

being $f_{stator}$ the fundamental frequency of the stator, g an integer, Q the number of slots of the stator and p the number of pole pairs.

In the case where the permanent magnet generator is synchronized to the network but not coupled thereto only the values of electrical variables and vibration at a same rotation speed will be taken into account for the calculation. (i.e. the analysis will be carried out at iso-speed). In this case the generator does not inject active power to the network and pure reactive power is used for operating the generator.

When the generator is coupled to the network only the values of electrical variables and vibration at a same rotation speed and at a same power will be taken into account for the calculation (i.e. the analysis will be carried out at iso-speed and iso-power).

C) Squirrel Cage Generators c1) The inverse component of the stator voltage at one or more of the following frequencies: fundamental frequency of the stator; an integer multiple of the inverse component of the fundamental frequency of the stator; an integer multiple of the direct component of the fundamental frequency of the stator.

c2) The inverse component of the stator current at one or more of the following frequencies: fundamental frequency of the stator; an integer multiple of the inverse component of the fundamental frequency of the stator; an integer multiple of the direct component of fundamental frequency the stator; frequencies defined by the formula $\pm nf_{sw} \pm mf_{stator}$, being n and m integer numbers, $f_{sw}$ the switching frequency of the converter and $f_{stator}$ the fundamental frequency of the stator.

c3) The mentioned vibrations at one or more of the following frequencies:

frequencies multiple of the frequency of the electrical network; frequencies defined by the formula $$f_{stator}\left[\pm 1 + \frac{\pm gQ}{p}(1-s)\right],$$

being $f_{stator}$ the fundamental frequency of the stator, g an integer, Q the number of slots of the stator, p the number of pole pairs and s the slip of the generator.

In the case where the squirrel cage generator is synchronized to the network but not coupled thereto only the values of electrical variables and vibration at a same rotation speed will be taken into account for the calculation. (i.e. the analysis will be carried out at iso-speed). In this case the generator does not inject active power to the network and pure reactive power is used for operating the generator.

When the generator is coupled to the network only the values of electrical variables and vibration at a same rotation speed and at a same power will be taken into account for the calculation (i.e. the analysis will be carried out at iso-speed and iso-power).

Although the present invention has been described in connection with various embodiments, it will be appreciated from the specification that various combinations of elements, variations or improvements therein may be made, and are within the scope of the invention as defined by the appended claims.

The invention claimed is:

1. A system comprising:
   (a) a wind turbine;
   (b) a generator comprising electrical insulation;
   (c) a converter;
   (d) an electrical variables measuring device that is configured and arranged to measure a voltage and a current in a rotor and a stator of the generator;
   (e) an electrical network, wherein the wind turbine is connected to the electrical network via the converter;
   (f) a sensor assembly comprising a first pair of sensors disposed on a first side of the generator and a second pair of sensors disposed on an opposite side of the generator, wherein the first pair of sensors comprises a first sensor configured and arranged to measure radial-vertical vibration in the first side of the generator and a second sensor configured and arranged to measure radial-horizontal vibration in the first side, and wherein the second pair of sensors comprises a third sensor configured and arranged to measure radial-vertical vibration in the opposite side of the generator and a fourth sensor configured and arranged to measure radial-horizontal vibration in the opposite side of the generator;
   (g) a vibration measuring device connected to the sensor assembly;
   (h) a data bus configured and arranged to receive in real-time (i) a data stream of measurements of electrical variables of the generator from the electrical variables measuring device and (ii) a data stream of measurements from the vibration measuring device; and
   (i) a computer connected to the data bus configured and arranged to (i) capture, in real-time during a predetermined time period, values of the electrical variables of the generators and values of the radial-vertical and radial-horizontal vibrations of the generator in at least one of the coupling side of the generator and the opposite side of the generator, (ii) obtain in real time a temporal evolution of inverse components of the electrical variables at one or more predetermined frequencies and a temporal evolution of the values of the vibrations at the one or more predetermined frequencies, (iii) identify a possible insulation fault in the generator when either the inverse component of the electrical variables or one of the radial-vertical and radial-horizontal vibration at one of the one or more predetermined frequencies exceeds an absolute threshold or a temporal increase threshold pre-set; wherein the one or more predetermined frequencies comprises (a) a frequency at which an insulation fault in the generator produces an imbalance of voltage and current variables in the rotor and stator that leads to an increase in an inverse component of said variables, and (b) a frequency at which an imbalance of currents caused by an insulation fault in the generator produces an electromagnetic imbalance that results in vibration of the generator such that the system can be used to identify an incipient fault in the electrical insulation of the generator.

2. The system according to claim 1, wherein:
the generator is a doubly fed generator;
the predetermined time period, in which the computer captures the values of the electrical variables and vibrations of the generator, is a period in which the generator is synchronized to the electrical network but not yet coupled to it;
the computer obtains a temporal evolution of one or more of the following variables in real-time:
1) an inverse component of a stator voltage at one or more of the following frequencies: a frequency of the electrical network; an integer multiple of an inverse component of the frequency of the electrical network; an integer multiple of the direct component of the frequency of the electrical network;
2) an inverse component of a rotor voltage at one or more of the following frequencies at a given speed: a fundamental frequency of the rotor; an integer multiple of an inverse component of the fundamental frequency of the rotor; an integer multiple of a direct component of the fundamental frequency of the rotor;
3) an inverse component of a rotor current at one or more of the following frequencies: a fundamental frequency of the rotor at a given speed; an integer multiple of an inverse component of the fundamental frequency of the rotor at a given speed; an integer multiple of the inverse component of the frequency of the electrical network; an integer multiple of the direct component of the frequency of the electrical network; frequencies defined by the formula $\pm nf_{sw} \pm mf_{rotor}$, with n and m being integer numbers, $f_{sw}$ a switching frequency of the converter and $f_{rotor}$ the fundamental frequency of the rotor;
4) the vibrations mentioned at one or more of the following frequencies: frequencies multiple of the frequency of the electrical network; frequencies defined by the formula $$f_{red}\left[\pm 1 + \frac{\pm gQ}{p}(1-s)\right],$$

with $f_{red}$ being the fundamental frequency of the electrical network, g an integer, Q a number of slots of the stator or the rotor, p a number of pole pairs, and s a slip of the generator.

3. The system according to claim 1, wherein:
the generator is a doubly fed generator;
the predetermined time period, in which the computer captures the values of the electrical variables and vibrations of the generator, is a period in which the generator is coupled to a grid and generating power;
a temporal evolution of one or more of the following variables at the same power is obtained in real-time:
1) an inverse component of a stator voltage at one or more of the following frequencies: a frequency of the electrical network, an integer multiple of an inverse component of the frequency of the electrical network, an integer multiple of a direct component of the frequency of the electrical network;
2) an inverse component of a stator current at one or more of the following frequencies: the frequency of the electrical network; an integer multiple of the inverse component of the frequency of the electrical network; an integer multiple of the direct component of the frequency of the electrical network;
3) an inverse component of a rotor voltage at one or more of the following frequencies at a given speed: a fundamental frequency of the rotor; an integer multiple of an inverse component of the fundamental frequency of the rotor; an integer multiple of a direct component of the fundamental frequency of the rotor;
4) an inverse component of a rotor current at one or more of the following frequencies: a fundamental frequency of the rotor at a given speed; an integer multiple of an inverse component of the fundamental frequency of the rotor at a given speed; an integer multiple of the inverse component of the frequency of the electrical network; an integer multiple of the direct component of the frequency of the electrical network; frequencies defined by the formula $\pm nf_{sw} \pm mf_{rotor}$, n and m being integer numbers, $f_{sw}$ a switching frequency of the converter and $f_{rotor}$ the fundamental frequency of the rotor;
5) the vibrations mentioned at one or more of the following frequencies: frequencies multiple of the frequency of the electrical network; frequencies defined by the formula $$f_{red}\left[\pm 1 + \frac{\pm gQ}{p}(1-s)\right],$$

with $f_{red}$ being the fundamental frequency of the electrical network, g an integer, Q a number of slots of the stator or the rotor, p a number of pole pairs, and s a slip of the generator.

4. The system according to claim 1, wherein:
the generator is a permanent magnet generator;
using values at a given speed when in the predetermined time period the generator is synchronized to the electrical network but not yet coupled to the electrical network and values at a given speed and at a given power when the generator is coupled to the electrical network, a temporal evolution of one or more of the following variables is obtained in real-time:
1) an inverse component of a stator voltage at one or more of the following frequencies: a fundamental frequency of a stator; an integer multiple of an inverse component of the fundamental frequency of the stator; an integer multiple of a direct component of the fundamental frequency of the stator;
2) an inverse component of a stator current at one or more of the following frequencies:
the fundamental frequency of the stator; the integer multiple of the inverse component of the fundamental frequency of the stator; the integer multiple of the direct component of fundamental frequency of the stator; frequencies defined by the formula $\pm nf_{sw} \pm mf_{stator}$, with n and m being integer numbers, $f_{sw}$ a switching frequency of the converter and $f_{stator}$ the fundamental frequency of the stator;

3) the mentioned vibrations at one or more of the following frequencies: frequencies multiple of a frequency of the electrical network; frequencies defined by the formula $$f_{stator}\left[\pm 1 + \frac{\pm gQ}{p}(1-s)\right],$$

with $f_{stator}$ being the fundamental frequency of the stator, g an integer, Q a number of slots of the stator, and p a number of pole pairs.

5. The system according to claim 1, wherein:
the generator is a squirrel cage generator;
using values at a given speed when in the time period mentioned the generator is synchronized to the electrical network but not yet couplet to the electrical network and values at a given speed and at a given power when the generator is coupled to the electrical network, the temporal evolution of one or more of the following variables is obtained in real-time:
1) an inverse component of a stator voltage at one or more of the following frequencies: a fundamental frequency of the stator; an integer multiple of the inverse component of the fundamental frequency of the stator; an integer multiple of the direct component of the fundamental frequency of the stator;
2) an inverse component of a stator current at one or more of the following frequencies: the fundamental frequency of the stator; the integer multiple of the inverse component of the fundamental frequency of the stator; an integer multiple of the direct component of fundamental frequency the stator; frequencies defined by the formula $\pm nf_{sw} \pm mf_{stator}$, n and m being integer numbers, $f_{sw}$ a switching frequency of the converter and $f_{stator}$ the fundamental frequency of the stator, and comprised between ±1 kHz and ±10 kHz;
3) the mentioned vibrations at one or more of the following frequencies: frequencies multiple of the frequency of the electrical network; frequencies defined by the formula $$f_{stator}\left[\pm 1 + \frac{\pm gQ}{p}(1-s)\right],$$

with $f_{stator}$ being the fundamental frequency of the stator, g an integer, Q a number of slots of the stator, p a number of pole pairs, and s a slip of the generator.

6. The system according to claim 1, wherein the electrical variables measuring device is incorporated in the converter.

7. The system according to claim 1, wherein the electrical variables measuring device is separately placed between and connected to the converter, the generator, and the data bus.

8. The system according to claim 1, wherein the generator has a cylindrical body, and wherein the first and second sensors are disposed along a circumference of a first base of the cylindrical body of the generator, and the third and fourth sensors are disposed along a circumference of a second based of the cylindrical body of the generator.

9. The system according to claim 1, wherein each of the first and second sensors and each of the third and fourth sensors are spaced 90° from each other along a circumference of the generator.

10. A method for preventing failure in electrical insulation of a generator of a wind turbine, wherein the generator is coupled to an electrical network through a converter, the method comprising the steps of:
- (a) providing the system of claim 1;
- (b) detecting whether there is a possible insulation fault in the electrical insulation of the generator, said detecting comprising the steps of: (i) capturing, in real-time during a predetermined time period, values of the electrical variables of the generators and values of the radial-vertical and radial-horizontal vibrations of the generator in at least one of the coupling side of the generator and the opposite side of the generator, (ii) obtaining in real time a temporal evolution of inverse components of the electrical variables at one or more predetermined frequencies and a temporal evolution of the values of the vibrations at the one or more predetermined frequencies, (iii) identifying a possible insulation fault in the generator when either the inverse component of the electrical variables or one of the radial-vertical and radial-horizontal vibration at one of the one or more predetermined frequencies exceeds an absolute threshold or a temporal increase threshold pre-set to identify an incipient fault in the electrical insulation of the generator;
- (c) if the detecting identifies a possible insulation fault in the electrical insulation of the generator, checking a state of the electrical insulation of the generator; and
- (d) if the checking identifies an insulation fault, activating corrective measures to repair the insulation fault.

* * * * *